United States Patent
Singer et al.

(10) Patent No.: US 11,738,125 B2
(45) Date of Patent: *Aug. 29, 2023

(54) SYSTEMS AND METHODS FOR ESTIMATING ULTRAFILTRATION RATES

(71) Applicant: Fresenius Medical Care Holdings, Inc., Waltham, MA (US)

(72) Inventors: Michael Singer, Natick, MA (US); Shawn Sobelman, Sacramento, CA (US); Robert Kossmann, Waltham, MA (US); Martin Joseph Crnkovich, Walnut Creek, CA (US); Roland Levin, San Ramon, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 105 days.

This patent is subject to a terminal disclaimer.

(21) Appl. No.: 17/320,901

(22) Filed: May 14, 2021

(65) Prior Publication Data
US 2021/0338908 A1 Nov. 4, 2021

Related U.S. Application Data

(63) Continuation of application No. 16/234,716, filed on Dec. 28, 2018, now Pat. No. 11,007,310.

(51) Int. Cl.
*A61M 1/16* (2006.01)
*G08B 21/18* (2006.01)

(52) U.S. Cl.
CPC ......... *A61M 1/1611* (2014.02); *G08B 21/182* (2013.01); *A61M 2205/18* (2013.01);
(Continued)

(58) Field of Classification Search
None
See application file for complete search history.

(56) References Cited

U.S. PATENT DOCUMENTS 6,602,424 B1 8/2003 Kraemer et al.
7,131,956 B1 11/2006 Pirazzoli et al.
(Continued)

FOREIGN PATENT DOCUMENTS

WO 98/19592 A1 5/1998
WO 2012/161744 A2 11/2012

OTHER PUBLICATIONS

International Search Report and Written Opinion in Application No. PCT/US2019/067038, dated Apr. 9, 2020, 12 pages.
(Continued)

*Primary Examiner* — Richard C Gurtowski
(74) *Attorney, Agent, or Firm* — Fish & Richardson P.C.

(57) ABSTRACT

Systems and methods for estimating the post-treatment ultrafiltration rate of a patient are provided. A medical device can be configured to determine an estimated post-treatment ultrafiltration rate based on one or more values associated with a patient prepared to undergo treatment with the medical device. The medical device can also be configured to compare the estimated post-treatment ultrafiltration rate with one or more threshold values. The medical device can be configured to have an alert module, which can be activated when the estimated post-treatment ultrafiltration rate exceeds the one or more threshold values.

20 Claims, 6 Drawing Sheets

(52) U.S. Cl.
CPC ... *A61M 2205/50* (2013.01); *A61M 2205/502* (2013.01); *A61M 2205/505* (2013.01); *A61M 2205/581* (2013.01); *A61M 2205/583* (2013.01); *A61M 2205/584* (2013.01); *A61M 2205/587* (2013.01)

(56) References Cited

U.S. PATENT DOCUMENTS

| | | |
|---|---|---|
| 8,105,260 B2 | 1/2012 | Tonelli et al. |
| 8,147,698 B2 | 4/2012 | Tolwani et al. |
| 8,945,036 B2 | 2/2015 | Szamosfalvi et al. |
| 9,526,820 B2 | 12/2016 | Beiriger et al. |
| 2009/0101566 A1 | 4/2009 | Crnkovich et al. |
| 2014/0102959 A1* | 4/2014 | Furuhashi ............ G16H 40/63 210/85 |
| 2016/0001000 A1 | 1/2016 | Awadalla |
| 2016/0378298 A1* | 12/2016 | Planas .................... A61M 1/36 715/771 |

OTHER PUBLICATIONS

Rose et al., "A dynamic Bayesian network for handling uncertainty i.n a decision support system adapted to the monitming of patients treated by hemodialysis," 17th IEEE International Conference on Tools with Artificial Intelligence, IEEE, Nov. 14, 2005, 6 pages.

PCT International Preliminary Report on Patentability in International Appln. No. PCT/US2019/067038, dated Jul. 8, 2021, 7 pages.

\* cited by examiner

SYSTEMS AND METHODS FOR ESTIMATING ULTRAFILTRATION RATES

CROSS-REFERENCE TO RELATED APPLICATIONS

This application is a continuation application of and claims priority to U.S. application Ser. No. 16/234,716, filed on Dec. 28, 2018.

TECHNICAL FIELD

This disclosure generally relates to systems and methods for estimating ultrafiltration rates.

BACKGROUND

Certain extracorporeal blood treatment systems, such as dialysis systems, use ultrafiltration to remove fluid from a patient undergoing dialysis treatment. Ultrafiltration generally refers to membrane filtration in which forces like pressure lead to a separation through a semipermeable membrane. Suspended solids and solutes of high molecular weight can be retained in a retentate, while water and low molecular weight solutes pass through the membrane in the filtrate. Ultrafiltration rate generally refers to the rate at which fluid is removed from a patient's body during a dialysis treatment. Excessive ultrafiltration rates may be a major source of morbidity and mortality for dialysis treatments. Because of these hazards, dialysis providers may be required to report ultrafiltration rates to agencies, such as to the Centers for Medicare & Medicaid Services (CMS) as part of quality incentive programs (QIPs).

SUMMARY

In at least one aspect of the present disclosure, a medical device is provided. The medical device includes a display device, a computer-readable medium that includes computer-executable instructions, one or more processors configured to execute the computer-executable instructions, an alert module configured to be communicatively coupled to the one or more processors and produce an alert, and a user interface configured to be communicatively coupled to the one or more processors. When the one or more processors are executing the computer-executable instructions, the one or more processors are configured to carry out operations to cause the display device to display the user interface, receive, through the user interface, one or more values associated with a user of the medical device, determine an estimated post-treatment ultrafiltration rate based on the one or more values, compare the predicted post-treatment ultrafiltration rate to an ultrafiltration rate threshold value, and cause the alert module to produce an alert if the predicted post-treatment ultrafiltration rate exceeds the ultrafiltration rate threshold value.

The one or more values associated with the user can include the user's current weight. The one or more values associated with the user can include a target dry weight of the user. The one or more values associated with the user can include an additional volume of fluid entering the user's body during a treatment session. The one or more values associated with the user can include an ultrafiltration time. The alert module can be configured to produce an audible alert. The alert module can be configured to produce a visual alert. The alert module can be configured to cause the display device to render a visual alert. The medical device can be a dialysis machine.

The ultrafiltration rate threshold value can be 13.0 mL/kg/hr. The one or more processors can be configured to dynamically determine the estimated post-treatment ultrafiltration rate while the user is undergoing treatment with the medical device. The one or more processors are configured to determine the estimated post-treatment ultrafiltration rate according to the formula:

$$\frac{(Current\ Weight - DryWeightTarget) * 1000 + AdditionalFluidVolume}{UFTime * DryWeightTarget}.$$

According to another aspect of the present disclosure, a method includes causing a display device of a medical device to display a user interface. The method includes, receiving, through the user interface, one or more values associated with a user of the medical device. The method includes determining a post-treatment ultrafiltration rate based on the one or more values. The method includes comparing the predicted post-treatment ultrafiltration rate to an ultrafiltration rate threshold value. The method includes causing an alert module associated with the medical device to produce an alert if the predicted post-treatment ultrafiltration rate exceeds the ultrafiltration rate threshold value.

The one or more values associated with the user can include the user's current weight. The one or more values associated with the user can include a target dry weight of the user. The one or more values associated with the user can include an additional volume of fluid entering the user's body during a treatment session. The one or more values associated with the user can include an ultrafiltration time. The alert can be an audible alert. The alert can be a visual alert. The alert can be rendered on the display device through the user interface. The medical device can be a dialysis machine.

The ultrafiltration rate threshold value can be 13.0 mL/kg/hr. The estimated post-treatment ultrafiltration rate can be determined dynamically while the user of the medical device is undergoing treatment with the medical device. Determining a post-treatment ultrafiltration rate can include using the formula $$\frac{(Current\ Weight - DryWeightTarget) * 1000 + AdditionalFluidVolume}{UFTime * DryWeightTarget}.$$

Implementations can include one or more of the following advantages. In some implementations, an extracorporeal blood treatment (ECBT) system is configured to estimate a post-treatment ultrafiltration rate for a patient before the patient undergoes dialysis treatment and/or while the patient is undergoing treatment. This can allow a medical provider to determine whether changes should be made to the treatment plan before or during the treatment process. In some implementations, the ECBT system is configured to generate an alert to notify the medical provider and/or the patient when the estimated ultrafiltration rate exceeds a threshold value. Thus, this disclosure provides an improvement to conventional ECBT systems that were previously incapable of determining projected ultrafiltration rates at treatment's end and alerting users when the ECBT system is being operated at high ultrafiltration rates before a patient undergoes medical treatment.

These and other aspects, features, and implementations can be expressed as methods, apparatus, systems, components, program products, means or steps for performing a function, and in other ways.

These and other aspects, features, and implementations will become apparent from the following descriptions, including the claims.

DETAILED DESCRIPTION

Figure 1:
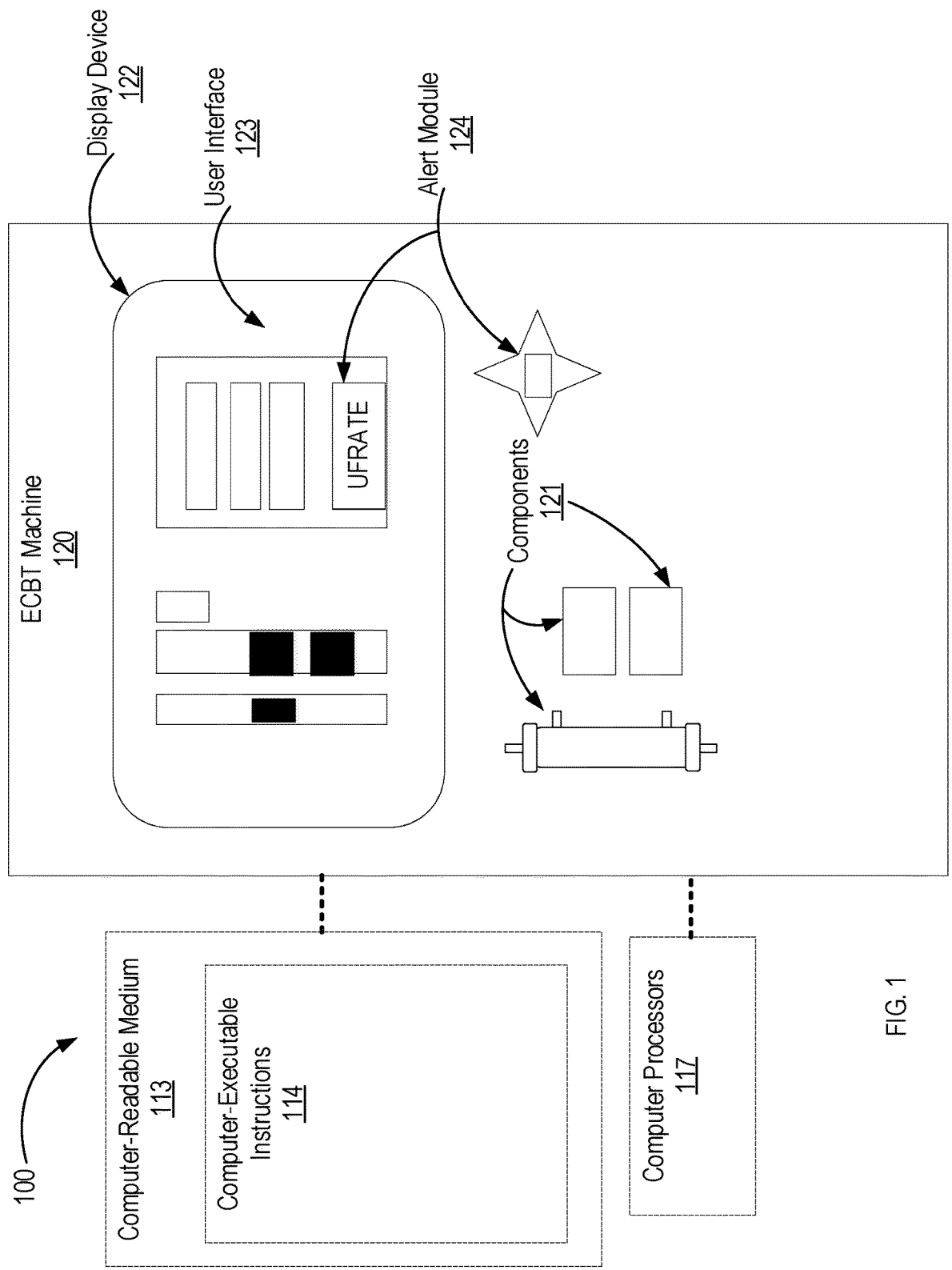
FIG. 1 shows an example of a system including an extracorporeal blood treatment machine to estimate ultrafiltration rates.

Conventional ultrafiltration rate calculations typically consider the patient's weight post-dialysis treatment. While, an actual post weight value is not available prior to or during an extracorporeal blood treatment (e.g., a dialysis treatment), it may be desirable to improve the effectiveness and performance of an extracorporeal blood treatment machine by providing the machine with means to predict the projected treatment end final individual ultrafiltration rate (UFR) of a patient before the patient undergoes treatment with the machine.

The present disclosure provides systems and methods for estimating the post-treatment ultrafiltration rate of a patient before the patient undergoes treatment. An extracorporeal blood treatment (ECBT) system can be configured to determine an estimated post-treatment ultrafiltration rate based on one or more values associated with a patient prepared to undergo treatment with the ECBT system. The ECBT system can also be configured to compare the estimated post-treatment ultrafiltration rate with one or more threshold values. The ECBT system can be configured to have an alert module, which can be activated when the estimated post-treatment ultrafiltration rate exceeds the one or more threshold values. These systems and methods can be implemented to improve conventional ECBT systems that were previously incapable of determining projected treatment end final individual UFRs. These systems and methods can also be implemented to improve use of conventional ECBT systems by enhancing clinical decision making at the point of care, and start of individual treatment, by ensuring the machines are able to provide projected treatment end final individual UFR in terms of volume (e.g., milliliters) per unit time (e.g., hours) per unit weight (e.g., kilograms) such that the individual determination can best be made regarding avoidance of high-risk ultrafiltration rates.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

In the drawings, specific arrangements or orderings of schematic elements, such as those representing devices, modules, instruction blocks and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood by those skilled in the art that such element represents one or multiple signal paths (e.g., a bus), as may be needed, to affect the communication.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

Several features are described hereafter that can each be used independently of one another or with any combination of other features. However, any individual feature may not provide any of the advantages discussed above or might only provide one of the advantages discussed above. Although headings are provided, data related to a particular heading, but not found in the section having that heading, may also be found elsewhere in this description.

FIG. 1 shows an example of a system 100 including an extracorporeal blood treatment (ECBT) machine 120 to estimate ultrafiltration rates. The ECBT machine 120 includes a display device 122 capable of rendering a user interface 123. The ECBT machine 120 also includes a plurality of components 121, an alert module 124, a computer-readable medium 113 and computer processors 117. The computer-readable medium 113 includes computer-executable instructions 114.

The ECBT machine 120 can be configured to provide one or more extracorporeal blood treatments, such as hemodialysis, hemofiltration, hemodiafiltration, ultrafiltration and/or other renal replacement therapies. In any case, the ECTB machine 120 is configured to remove fluid from a user (e.g., patient) of the ECBT machine 120. An example of a ECTB machine 120 is discussed later in more detail with reference to FIG. 3.

The display device 122 can be an electronic display device. The display device 122 can be configured to act as a touchscreen display device. In some implementations, the user interface 123 is a graphical user interface (GUI). The user interface 123 is configured to allow a user of the ECBT machine 120 to interact with the ECBT machine 120 through graphical icons and visual indicators. The user interface 123 can use a windows, icons, menus, pointer paradigm (WIMP) to allow a user to interact with the ECBT machine 120. In some implementations, the user interface 123 cooperates with the display device 122 to provide a user with a touchscreen GUI. Additionally, or alternatively, the user interface can include one or more input devices such as a mouse and/or keyboard communicatively coupled with the ECBT machine 120. The user interface 123 can also use a post-WIMP paradigm typically found in touchscreen-based GUIs. In some implementations, the user interface 123 is configured to display images in the form of still photographs and/or videos.

The user interface 123 can display information associated with the ECBT machine 120. For example, the user interface 123 can show graphical charts and values associated with arterial pressure readings, venous pressure readings, dialysate flow rates, temperature readings, blood pump rates, and so forth. In some implementations, the user interface 123 displays a value associated with an estimated ultrafiltration rate (e.g., Est UFR). In some implementations, the user interface 123 prompts a user (e.g., medical personnel, patient, etc.) to input one or more values associated with a user of the ECBT machine 120. In some implementations, the user interface 123 prompts the user to input the user's current weight, target dry weight, an additional volume of fluid, and/or ultrafiltration time. A target dry weight refers to the desired weight of a patient post-dialysis treatment and can be generally associated with a predicted weight of a patient who is euvolemic (e.g., in normal fluid balance, such as if the patient were in a state of normal, healthy kidney function where normal urine output were present). Additional volume of fluid may refer to water, saline treatment, and so forth, which a patient may receive while undergoing dialysis treatment. Ultrafiltration time generally refers to the amount of time a patient is expected to undergo dialysis treatment. As discussed later, these values can be used to determine an estimated ultrafiltration rate. The user can enter the values using the touchscreen of the display device 122, a keyboard, and/or any other device suitable for interacting with the user interface 123.

The computer-readable medium 113 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In some implementations, the computer-readable medium 113 includes code-segment having executable instructions. In some implementations, the computer-readable medium 113 stores information corresponding to the components 121 of the ECBT machine 120.

The alert module 124 is configured to produce an audible alert and/or a visual alert. For example, the alert module 124, can include means for producing flashing/pulsed light (e.g., light bulbs, light-emitting diodes, etc.). In some implementations, the pulsed light is red. In some implementations, the alert module includes speakers. In some implementation, the audible alert includes tones having one of several frequencies. In some implementations, the alert module 124 is integrated with the user interface 123. For example, the user interface 123 can display boxes, such as a box that displays an estimated ultrafiltration rate, which can flash certain colors that may command the attention of a user of the ECBT machine 120. The alert module 124 can also include means of providing a physical alert. For example, the alert module 124 can include mechanisms configured to vibrate the ECBT machine 120 and/or be placed on the body of a patient of the ECBT machine 120 to impart vibrations on the patient's body.

The computer processors 117 are communicatively coupled to the display device 122, the user interface 123, and/or the alert module 124. In some implementations, the computer processors 117 include a general purpose processor. In some implementations, the computer processors 117 include a central processing unit (CPU). In some implementations, the computer processors 117 include at least one application specific integrated circuit (ASIC). The computer processors 117 can also include general purpose programmable microprocessors, special-purpose programmable microprocessors, digital signal processors (DSPs), programmable logic arrays (PLAs), field programmable gate arrays (FPGA), special purpose electronic circuits, etc., or a combination thereof. The computer processors 117 are configured to execute program code means such as the computer-executable instructions.

When the computer processors 117 execute the computer-executable instructions, the computer processors 117 carry out one or more operations. In some implementations, when the computer processors 117 are executing the computer-executable instructions, the computer processors 117 carry out operations to cause the display device 122 to display the graphical user interface 123. As previously indicated, the graphical user interface 123 can prompt the user to enter one or more values associated with a patient undergoing treatment using the ECBT machine 120.

When the computer processors 117 are executing the computer-executable instructions, the computer processors 117 carry out operations to receive, through the user interface 123, one or more values associated with a user of the ECBT machine 120. For example, as indicated earlier, a patient or physician can enter values associated with a patient undergoing treatment with the ECBT machine 120, such as the patient's current weight, target dry weight, an additional volume of fluid, and/or ultrafiltration time. In some implementations, the values can be received by other sensor devices external and/or internal to the ECBT machine 120. For example, the patient's current weight can be received from a weight sensor (e.g., scale) configured to measure the weight of the patient. The weight sensor can be integrated within the ECBT machine 120 (e.g., underneath a seating arrangement) or it can be external to the ECBT machine 120.

When the computer processors 117 are executing the computer-executable instructions, the computer processors 117 carry out operations to determine an estimated post-treatment ultrafiltration rate based on the one or more values.

For example, in some implementations, the computer processors 117 determines an estimated post-treatment ultrafiltration rate according to the following:

$$\text{Estimated } UFR = \frac{(\text{Current Weight} - DryWeightTarget) * 1000 + AdditionalFluidVolume}{UFTime * DryWeightTarget},$$

where CurrentWeight is the weight of the patient at the time before the patient undergoes treatment, DryWeightTarget is the desired weight of the patient after undergoing ultrafiltration treatment, AdditionalFluidVolume is an estimated volume of fluid which a patient may receive while undergoing treatment, and UFTime is the amount of time the patient will undergo ultrafiltration. In some implementations, weight is defined in terms of kilograms, volume is defined in terms of milliliters, and time is defined in terms of hours. However, each variable may be defined using other metrics, such as pounds, liters, and seconds, respectively. In some implementations, the computer processors 117 determine an estimated post-treatment ultrafiltration rate before a patient begins treatment. In some implementations, the computer processors 117 determine an estimated post-treatment ultrafiltration rate during treatment. In some implementation, the computer processors 117 determine an estimated post-treatment ultrafiltration rate dynamically during treatment. For example, the computer processors 117 can continuously updated the estimated post-treatment ultrafiltration rate based on changed variables, such as a change in the time of ultrafiltration and/or change in volume of fluid received by the patient.

When the computer processors 117 are executing the computer-executable instructions 114, the computer processors 117 carry out operations to compare the estimated post-treatment ultrafiltration rate with an ultrafiltration rate threshold value. The ultrafiltration rate threshold value can be based on, for example, healthcare standards and/or safety considerations. In some implementations, the ultrafiltration rate threshold value is 13.0 mL/kg/hr. In some implementations, the user interface 123 is configured to prompt a user to input an ultrafiltration rate threshold value. In some implementations, the ultrafiltration rate threshold value is a set default value initialized by a manufacturer or medical care personnel.

When the computer processors 117 are executing the computer-executable instructions 114, the computer processors 117 carry out operations to cause the alert module 124 to produce an alert if the estimated post-treatment ultrafiltration rate exceeds the ultrafiltration rate threshold. For example, if the estimated post-treatment ultrafiltration rate exceeds 13.0 mL/kg/hr, the alert module 124 can be caused to produce one or more visual alerts (e.g., flashing red light) and/or one or more audible alerts (e.g., high-pitched beeping sound). The alert module 124 can also impart vibrations on the ECBT machine 120 or the patient's body. In some implementations, the alert module 124 causes the user interface 123 to display a visual alert. Alternatively, or additionally, the alert module 124 includes a biofeedback algorithm, which is capable of controlling one or more operating parameters of the ECBT machine 120 by adjusting the one or more operating parameters such that the estimated UFR is reduced.

Figure 2:
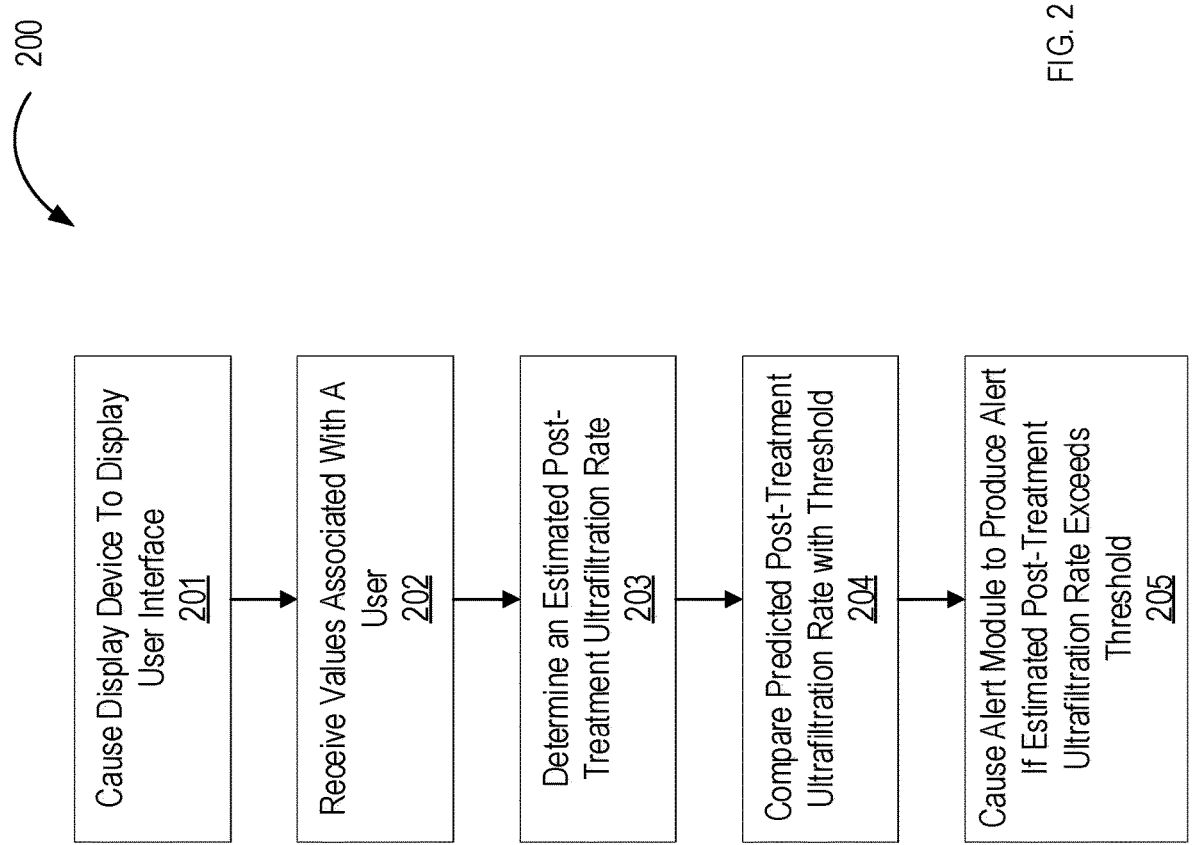
FIG. 2 shows a flowchart depicting an example of a method 200 for estimating ultrafiltration rates according to one or more embodiments of the present disclosure.

FIG. 2 shows a flowchart depicting an example of a method 200 for estimating ultrafiltration rates according to one or more embodiments of the present disclosure. For illustrative purposes, the system 100 for estimating ultrafiltration rates performs the method 200a. However, the method 200a may be performed by other systems that allow for estimating filtration rates. The method 200a includes causing a display device to display a user interface (block 201), receiving values associated with a user (block 202), determining an estimated post-treatment ultrafiltration rate (block 203), comparing the predicted post-treatment ultrafiltration rate with a threshold value (block 204) and causing an alert module to produce an alert if the estimated post-treatment ultrafiltration rate exceeds the threshold value (block 205).

At block 201, the computer processors 117 carry out operations to cause display device to display the graphical user interface 123. As previously indicated, the graphical user interface 123 can prompt the user to enter one or more values associated with a patient undergoing treatment using the ECBT machine 120.

At block 202, the computer processors 117 carry out operations to receive, through the user interface 123, one or more values associated with a user of the ECBT machine 120. For example, as indicated earlier, a patient or physician, can enter values associated with a patient undergoing treatment with the ECBT machine 120, such as the patient's current weight, target dry weight, an additional volume of fluid, and/or ultrafiltration time. In some implementations, the values can be received by other sensor devices external and/or internal to the ECBT machine 120. For example, the patient's current weight can be received from a weight sensor (e.g., scale) configured to measure the weight of the patient. The weight sensor can be integrated within the ECBT machine 120 (e.g., underneath a seating arrangement) or it can be external to the ECBT machine 120.

At block 203, the computer processors 117 carry out operations to determine an estimated post-treatment ultrafiltration rate based on the one or more values. For example, in some implementations, the computer processors 117 determines an estimated post-treatment ultrafiltration rate according to the following:

$$\text{Estimated } UFR = \frac{(\text{Current Weight} - DryWeightTarget) * 1000 + AdditionalFluidVolume}{UFTime * DryWeightTarget},$$

where CurrentWeight is the weight of the patient at the time before the patient undergoes treatment, DryWeightTarget is the desired weight of the patient after undergoing ultrafiltration treatment, AdditionalFluidVolume is an estimated volume of fluid which a patient may receive while undergoing treatment, and UFTime is the amount of time the patient will undergo ultrafiltration. In some implementations, the computer processors 117 determine an estimated post-treatment ultrafiltration rate before a patient begins treatment. In some implementations, the computer processors 117 determine an estimated post-treatment ultrafiltration rate during treatment. In some implementation, the computer processors 117 determine an estimated post-treatment ultrafiltration rate dynamically during treatment. For example, the computer processors 117 can continuously updated the estimated post-treatment ultrafiltration rate based on changed variables, such as a change in the time of ultrafiltration and/or change in volume of fluid received by the patient.

At block 204, the computer processors 117 carry out operations to compare the estimated ultrafiltration rate with an ultrafiltration rate threshold value. The ultrafiltration rate threshold value can be based on, for example, healthcare standards and/or safety considerations. In some implementations, the ultrafiltration rate threshold value is 13.0 mL/kg/hr. In some implementations, the user interface 123 is configured to prompt a user to input an ultrafiltration rate threshold value. In some implementations, the ultrafiltration rate threshold value is a set default value initialized by a manufacturer or medical care personnel.

At block 205, the computer processors 117 carry out operations to cause the alert module 124 to produce an alert if the estimated post-treatment ultrafiltration rate exceeds the ultrafiltration rate threshold. For example, if the estimated post-treatment ultrafiltration rate exceeds 13.0 mL/kg/hr, the alert module 124 can be caused to produce one or more visual alerts (e.g., flashing red light) and/or one or more audible alerts (e.g., high-pitched beeping sound). The alert module 124 can also impart vibrations on the ECBT machine 120 or the patient's body. In some implementations, the alert module 124 causes the user interface 123 to display a visual alert.

Figure 3:
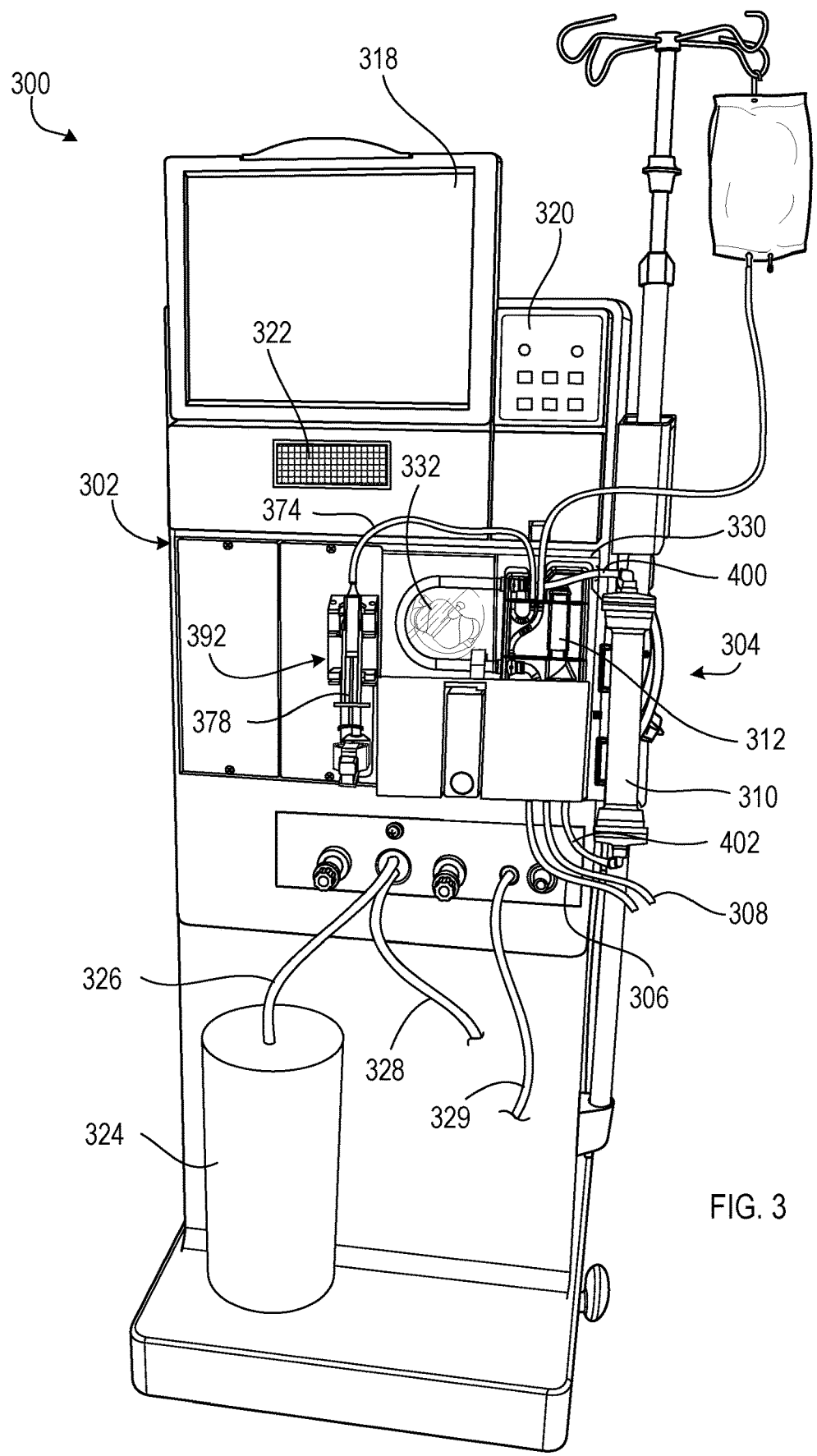
FIG. 3 is a front perspective view of a hemodialysis system.
Figure 4:
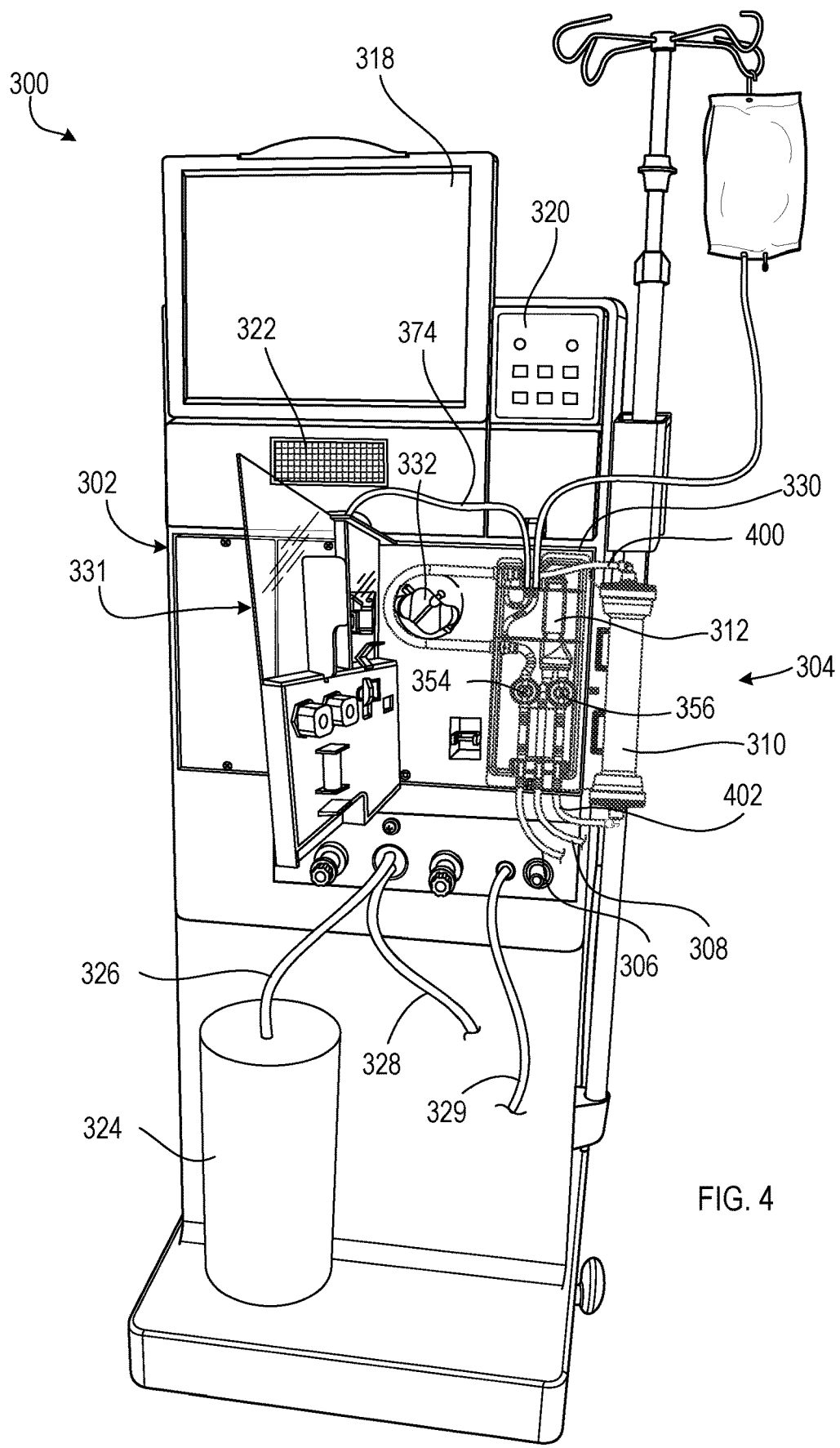
FIG. 4 is a front perspective view of the hemodialysis system of FIG. 3 with a door of a module of the hemodialysis system in an open position to expose a blood component secured to the module.

FIG. 3 is a front perspective view of a hemodialysis system 300. FIG. 4 is a front perspective view of the hemodialysis system 300 of FIG. 3 with a door of a module of the hemodialysis system in an open position to expose a blood component secured to the module. Referring to FIGS. 3 and 4, the hemodialysis system 300 includes a hemodialysis machine 302 to which a disposable blood component set 304 that forms a blood circuit is connected. In some implementations, the hemodialysis machine 302 is the ECBT machine 120 of FIG. 1 and is configured to perform the method 200 for estimating ultrafiltration rates as discussed earlier with reference to FIG. 2.

During hemodialysis, arterial and venous patient lines 306, 308 of the blood component set 304 are connected to a patient and blood is circulated through various blood lines and components, including a dialyzer 310, of the blood component set 304. At the same time, dialysate is circulated through a dialysate circuit formed by the dialyzer 310 and various other dialysate components and dialysate lines connected to the hemodialysis machine 302. Many of these dialysate components and dialysate lines are located inside the housing of the hemodialysis machine 302, and are thus not visible in FIGS. 3 and 4. The dialysate passes through the dialyzer 310 along with the blood. The blood and dialysate passing through the dialyzer 310 are separated from one another by a semi-permeable structure (e.g., a semi-permeable membrane and/or semi-permeable microtubes) of the dialyzer 310. As a result of this arrangement, toxins are removed from the patient's blood and collected in the dialysate. The filtered blood exiting the dialyzer 310 is returned to the patient. The dialysate that exits the dialyzer 310 includes toxins removed from the blood and is commonly referred to as "spent dialysate." The spent dialysate is routed from the dialyzer 310 to a drain.

The hemodialysis machine 302 includes a touch screen 318 and a control panel 320. The touch screen 318 and the control panel 320 allow a user (e.g., a medical provider, patient, etc.) to input various different treatment parameters to the hemodialysis machine 302 and to otherwise control the hemodialysis machine 302. In addition, the touch screen 318 serves as a display to convey information to the user of the hemodialysis system 300. A speaker 322 is positioned below the touch screen 318 and functions to provide audio signals to the user of the system 300. Thus, the hemodialysis machine 302 is capable of providing both visual alerts via the touch screen 318 and audio alerts via the speaker 322 to the user of the system 300 during use. While the speaker 322 has been described as being positioned below the touch screen 318, the speaker 322 could be positioned at any of various other locations on the hemodialysis machine 302.

In some implementations, the touch screen 318 is an embodiment of the display device 122 and the user interface 123 of FIG. 1. For example, the touch screen 318 can render the user interface 123 to allow a user to input the one or values associated with the patient/user for determining an estimated UFR. For example, before a dialysis treatment begins, the touch screen 318 can display graphics prompting a user to input values for estimating an UFR, and based on those values, the hemodialysis machine 302 can determine an estimated UFR as described earlier with reference to FIG. 2. The touch screen 318 can then display the estimated UFR. In some implementations, the visual alerts provided by the touch screen 318 are part of the alert module 124 of FIG. 1, where the touch screen 318 provides the visual alert (e.g., flashing red light) in response to the estimated UFR exceeding the UFR threshold value. In some implementations, the speaker 322 is part of the alert module 124, where the speaker 322 provides audible alerts in response to the estimated UFR exceeding the UFR threshold.

A dialysate container 324 is connected to the hemodialysis machine 302 via a dialysate supply line 326. A drain line 328 and an ultrafiltration line 329 also extend from the hemodialysis machine 302. The dialysate supply line 326, the drain line 328, and the ultrafiltration line 329 are fluidly connected to the various dialysate components and dialysate lines inside the housing of the hemodialysis machine 302 that form part of the dialysate circuit. During hemodialysis, the dialysate supply line 326 carries fresh dialysate from the dialysate container 324 to the portion of the dialysate circuit located inside the hemodialysis machine 302. As noted above, the fresh dialysate is circulated through various dialysate lines and dialysate components, including the dialyzer 310, that form the dialysate circuit. As the dialysate passes through the dialyzer 310, it collects toxins from the patient's blood. The resulting spent dialysate is carried from the dialysate circuit to a drain via the drain line 328. When ultrafiltration is performed during treatment, a combination of the spent dialysate and excess fluid drawn from the patient is carried to the drain via the ultrafiltration line 329.

The blood component set 304 is secured to a module 330 attached to the front of the hemodialysis machine 302. The module 330 includes a blood pump 332 capable of driving blood through the blood circuit. The module 330 also includes various other instruments capable of monitoring the blood flowing through the blood circuit. The module 330 includes a door 331 that when closed, as shown in FIG. 3, cooperates with the front face of the module 330 to form a compartment sized and shaped to receive the blood component set 304. In the closed position, the door 331 presses certain blood components of the blood component set 304 against corresponding instruments exposed on the front face of the module 330.

The dialysate circuit is formed by multiple dialysate components and dialysate lines positioned inside the housing of the hemodialysis machine 302 as well as the dialyzer 310, a dialyzer inlet line 400, and a dialyzer outlet line 402 that are positioned outside of the housing of the hemodialysis machine 302. The dialyzer inlet line 400 includes a connector adapted to connect to one end region of the dialyzer 310, and the dialyzer outlet line 402 includes a connector adapted to connect to another end region of the dialyzer 310.

Figure 5:
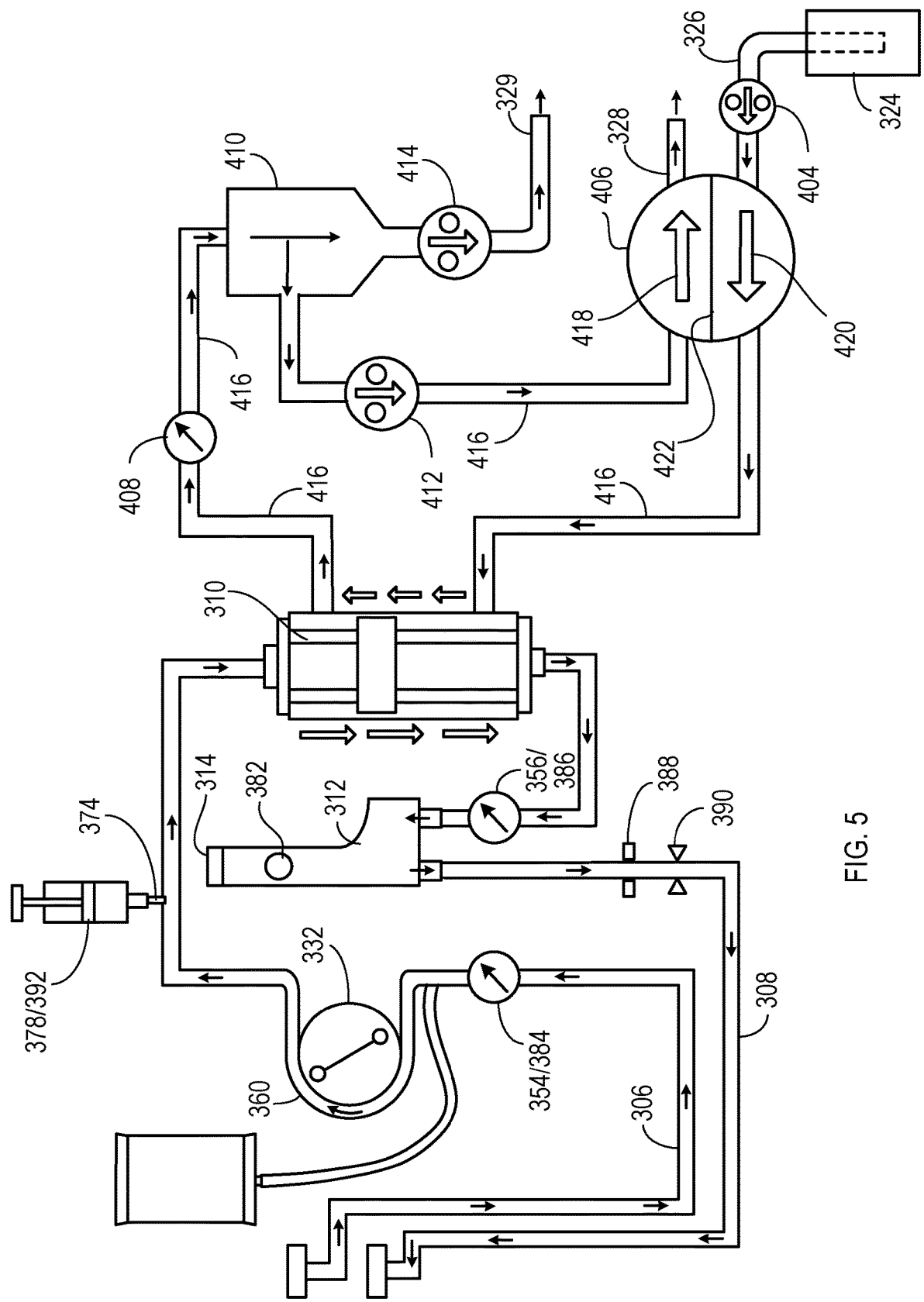
FIG. 5 is a schematic showing the flow paths of fluids into, through, and out of the blood circuit and the dialysate circuit of the hemodialysis system.

FIG. 5 is a schematic showing the flow paths of fluids into, through, and out of the blood circuit and the dialysate circuit of the hemodialysis system 300. The dialysate components of the dialysate circuit that are located inside the housing of the hemodialysis machine 302 include a first dialysate pump 404, a balancing device 406, a pressure sensor 408, an equalizing chamber 410, a second dialysate pump 412, and an ultrafiltration pump 414. These dialysate components are fluidly connected to one another via a series of dialysate lines 416.

The dialysate pump 404 is capable of pumping dialysate to the balancing chamber 406 via the dialysate supply line 326. In some implementations, the dialysate pump 404 is a peristaltic pump. However, any various other types of pumps can alternatively or additionally be used. Examples of other suitable types of pumps include diaphragm pumps and gear pumps.

The balancing device 406 includes a spherical chamber that is divided into a first chamber half 418 and a second chamber half 420 by a flexible membrane 422. As fluid flows into the first chamber half 418, fluid is forced out of the second chamber half 420, and vice versa. This balancing device construction helps to ensure that the volume of fluid entering the balancing device 406 is equal to the volume of fluid exiting the balancing device 406. This helps to ensure that the volume of fresh dialysate entering the dialysate circuit is equal to the volume of spent dialysate exiting the dialysate circuit when desired during treatment, as described in greater detail below.

During hemodialysis, the dialysate exiting the second chamber half 420 is directed through the dialyzer 310 toward the equalizing chamber 410. The pressure sensor 408 located along the dialysate line 416 connecting the dialyzer 310 to the equalizing chamber 410 is adapted to measure the pressure of the spent dialysate exiting the dialyzer 310. Any of various different types of pressure sensors capable of measuring the pressure of the spent dialysate passing from the dialyzer 310 to the equalizing chamber 410 can be used.

The spent dialysate collects in the equalizing chamber 410. The dialysate pump 412 is configured to pump the spent dialysate from the equalizing chamber 410 to the first chamber half 418 of the balancing device 406. In some implementations, the dialysate pump 412 is a peristaltic pump. However, any various other types of pumps can alternatively or additionally be used. Examples of other suitable types of pumps include diaphragm pumps and gear pumps. As the first chamber half 418 of the balancing device 406 fills with the spent dialysate, fresh dialysate within the second chamber half 420 is expelled toward dialyzer 310. Subsequently, as the second chamber half 420 is refilled with fresh dialysate, the spent dialysate within the first chamber half 418 is forced through the drain line 328 to the drain.

The ultrafiltration line 329 is connected to an outlet of the equalizing chamber 410. The ultrafiltration pump 414 is operatively connected to the ultrafiltration line 329 such that when the ultrafiltration pump 414 is operated, spent dialysate can be pulled from the equalizing chamber 410 and directed to the drain via the ultrafiltration line 329. Operation of the ultrafiltration pump 414 while simultaneously operating the dialysate pump 412 causes increased vacuum pressure within the dialysate line 416 connecting the equalizing chamber 410 to the dialyzer 310, and thus creates increased vacuum pressure within the dialyzer 310. As a result of this increased vacuum pressure, additional fluid is pulled from the blood circuit into the dialysate circuit across the semi-permeable structure (e.g., semi-permeable membrane or semi-permeable microtubes) of the dialyzer 310. In certain implementations, the ultrafiltration pump 414 is a peristaltic pump. However, any various other types of pumps can alternatively or additionally be used. Examples of other suitable types of pumps include diaphragm pumps and gear pumps.

Figure 6:
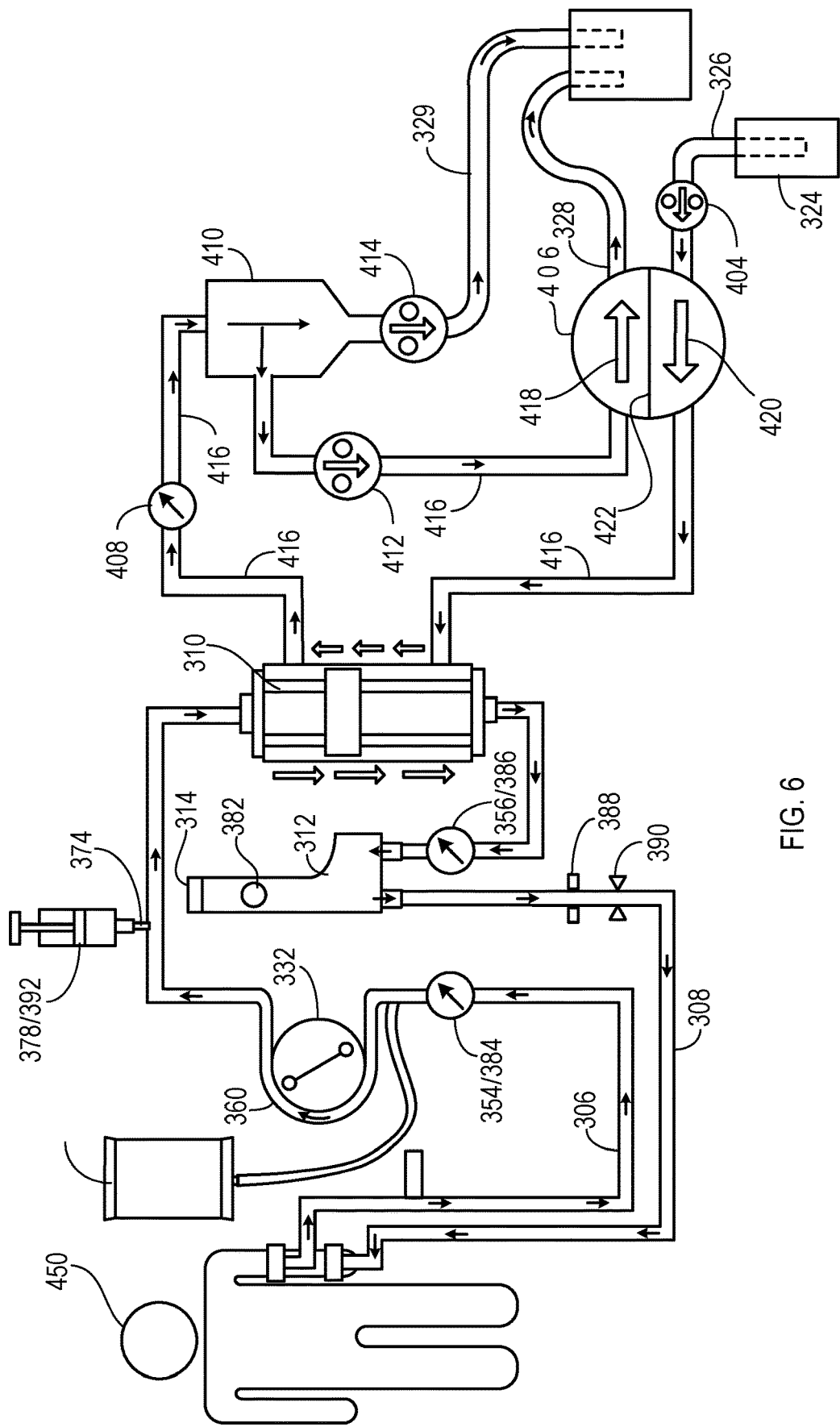
FIG. 6 is a schematic of fluid flow through the blood circuit and dialysate circuit of the hemodialysis system of FIG. 3 when the hemodialysis system is connected to a patient for treatment.

FIG. 6 is a schematic of fluid flow through the blood circuit and dialysate circuit of the hemodialysis system 300 of FIG. 3 when the hemodialysis system 300 is connected to a patient for treatment. During hemodialysis treatment, the blood pump 332 is activated causing blood to circulate through the blood circuit. The blood follows the same basic route as the route of the saline described above and, for the most part, pushes the residual saline in the blood circuit through the various blood components and blood lines and back to the patient. The blood is drawn from the patient 450 via the arterial patient line 306 and flows to the arterial pressure sensor capsule 354. The arterial pressure sensor 384 on the front face of the module 330 aligns with the pressure sensor capsule 354 and measures the pressure of the blood flowing through the blood circuit on the arterial side. The blood then flows through the U-shaped pump line 360, which is operatively engaged with the blood pump 332. From the pump line 360, the blood flows to the dialyzer 310. After exiting the dialyzer 310, the blood flows through a venous pressure sensor capsule 356 where the pressure of the blood on the venous side is measured by the associated pressure sensor 386 on the front face of the module 330 (shown in FIG. 9).

In certain implementations, a drug, such as heparin, is injected into the blood via a drug delivery line 374 by activating a drug pump 392. Injecting heparin into the blood can help to prevent blood clots from forming within the blood circuit. Other types of drugs can alternatively or additionally be injected from the syringe 378 into the blood circuit. Examples of such drugs include vitamin D and iron supplements, such as Venofer® and Epogen®.

Next, the blood flows through an entry port of the air release device 312 in which any gas, such as air, in the blood can escape. When the blood enters a chamber of the air release device 312, the blood forces the saline at the bottom of the chamber, which remains in the chamber from the priming procedure, through an exit port of the air release device 312. However, the blood does not displace all of the saline within the chamber. Because of the size and shape of the chamber, the blood enters the chamber and only traverses part of the height of the chamber before flowing back down and exiting the exit port. The interface between the saline and the blood delineates the furthest extent of the vast majority of the blood within the chamber. Because blood and saline are not immiscible, there is some amount of mixing between the two fluids around the interface.

The saline substantially prevents the blood from contacting a membrane of the vent assembly 314. However, some blood can be present in the saline without hindering treatment. That is, the saline need not be completely free of blood for the air release device 312 to both allow gas (e.g., from air bubbles in the blood) to vent from the blood circuit and retain the liquid within the blood circuit. The solution that is mostly saline protects the membrane of the vent assembly 314 from becoming coated with protein, which could clog the vent assembly 314 and reduce the ability of the air release device 312 to vent air and other gases from the chamber of the air release device 312 to the atmosphere. If the chamber of the release device 312 is sufficiently elongated, the blood does not mix with the saline at the top portion of the chamber 316 because the saline remains relatively stagnant as the blood flows through the chamber.

Any unbound gas, or air, that is in the blood, such as air that is introduced by the dialyzer 310 or syringe 378, rises as tiny air bubbles within the blood and saline until the air eventually vents out through the vent assembly 314. The blood travels up and over the dam 346 rather than straight across the bottom of the chamber and out the exit port. By directing the flow of blood upwards, the blood with air is not able to flow in and directly back out of the chamber 316 without flowing upwards to at least a height greater then the height of the dam 346. The surface area of the dam 346 and the inner walls of the chamber encourage air, including microbubbles, to separate from the blood and exit the blood circuit through the vent assembly 314. After exiting the air release device 312, the blood travels through the venous patient line 308 and back to the patient.

During hemodialysis, fresh dialysate is pumped into the dialysate circuit from the dialysate container 324 via the dialysate supply line 326 by running the dialysate pump 404. The fresh dialysate enters the second chamber half 420 of the balancing device 406. As spent dialysate enters the first chamber half 418 of the balancing device 406, the fresh dialysate is forced out of the second chamber half 420 and toward the dialyzer 310 via the dialysate line 416. The dialysate passes through the dialyzer 310 at the same time that the patient's blood is passed through the dialyzer 310 on an opposite side of the semi-permeable structure of the dialyzer 310. As a result, toxins, such as urea, are transferred across a permeable structure (e.g., permeable membrane and/or permeable microtubes) of the dialyzer 310 from the patient's blood to the dialysate, and those toxins collect in the dialysate forming spent dialysate. The spent dialysate exiting the dialyzer 310 is circulated through the dialysate circuit to the equalizing chamber 410. The dialysate pump 412 draws spent dialysate from the equalizing chamber 410 and delivers it to the first chamber half 418 of the balancing device 406. As the spent dialysate fills the first chamber half 418, fresh dialysate within the second chamber have 420 is delivered to the dialyzer 310. As the second chamber half 420 is subsequently refilled with fresh dialysate, the spent dialysate within the first chamber half 418 is forced out of the balancing device 406 and into a drain via the drain line 328. The balancing device 406 balances the dialysate entering the dialysate circuit with the dialysate exiting the dialysate circuit to ensure that a substantially constant volume of dialysate remains within the dialysate circuit when ultrafiltration is not being performed.

In certain treatments, an ultrafiltration process is performed to remove excess fluid from the patient's blood. During ultrafiltration, a pressure gradient is created across the permeable structure between the dialysate side and the blood side of the dialyzer 310 by running the ultrafiltration pump 414. As a result, fluid is drawn across the semi-permeable structure of the dialyzer 310 from the blood circuit to the dialysate circuit. Spent dialysate, including the toxins and excess fluid drawn from the patient, is drawn from the equalizing chamber 410 by the ultrafiltration pump 414 and is delivered to the drain via the ultrafiltration line 329.

While certain embodiments have been described above, other embodiments are possible.

While the methods described above involve activating an audio alarm and visual arm in response to detecting a malfunctioning device, an audio alarm alone or a visual alarm alone can alternatively be used to alert the operator of the system to the malfunctioning device.

In some implementations, the air release device 312 and at least one of the other blood components and blood lines (e.g., all of the other blood components and blood lines) are incorporated into an integrated blood component set. The various components of the integrated blood circuit can be formed together in one assembly or integrated molding rather than discrete separate or modular devices. The integrated blood component set can be adapted to removably seat into the module 330 of the hemodialysis machine 302 in a manner similar to the blood component set 304 described above.

While the various blood components have been described as being incorporated into an integrated blood component set, the blood components can alternatively be secured to a carrier body of the hemodialysis machine 302 or connected to one another by blood lines alone. In such implementations, the blood components would be individually secured to the hemodialysis machine 302 (e.g., the module 330 of the hemodialysis machine 302) prior to treatment. The functionality of the blood components would be similar to the functionality of those blood components discussed above. Suitable blood component sets and their related components are described in greater detail in U.S. Patent Application Publication No. 2009/0101566, entitled "Dialysis Systems and Related Components," which is incorporated by reference herein.

While the dialysate circuit has been described as being partially integrated with the hemodialysis machine 302, the dialysate circuit can alternatively be formed by a dialysate component set that can be removably secured to a hemodialysis machine during use. In some implementations, the dialysate component set is in the form of a cassette that can be inserted into a drawer of the hemodialysis machine in a manner such that the cassette operatively engages components of the hemodialysis machine when the drawer is closed. Such a dialysate component sets is described, for example, in U.S. Patent Application No. 61/231,220, entitled "Dialysis Systems, Components, and Methods" and filed on Aug. 4, 2009, which is incorporated by reference herein.

While the dialysate supply line 326 has been described as carrying fresh dialysate, the hemodialysis machine 302 can alternatively be configured to generate dialysate from acid concentrate, bicarbonate concentrate, and purified water. For example, in some implementations, the dialysate supply line 326 is coupled to an acid concentrate source, the drain line 328 is coupled to bicarbonate concentrate source, and the ultrafiltration line 329 is coupled to a drain. In such implementations, the hemodialysis machine 302 further includes a purified water inlet. The acid concentrate and the bicarbonate concentrate can be introduced into the purified water to generate dialysate online.

While the air release device 312 of the extracorporeal blood circuit discussed above has blood entry port and a blood exit port in the bottom of the device, in some implementations, the air release device includes a blood entry port at the top of the device and a blood exit port at the bottom of the device.

While the dialysate circuit of the ECBT machine 302 has been described as including aa balance chamber, a fresh dialysate pump, a spent dialysate pump, and a UF pump, in some implementations, the dialysate circuit includes no balance chamber or separate UF pump. In such implementations, for example, the dialysate circuit can include a fresh dialysate pump and a spent dialysate pump, such as impeller pumps, whose speeds can be controlled to achieve a desired UF rate.

While the ECBT machine 120 and the hemodialysis machine 302 have been described as including a touch screen, it should be appreciated that any of the ECBT/hemodialysis machines described herein can alternatively be provided with a conventional screen and an associated control panel, mouse and/or keyboard to allow the user to input data. Alternatively or additionally, the hemodialysis machine can be equipped with a scratch pad and/or touch buttons that permit the user to input data.

While certain visual alarms have been described as being displayed via the touch screen 318, the visual alarms can be displayed using other types of devices. For example, in implementations in which the dialysis machine includes a traditional screen (i.e., a non-touch screen) along with a separate device, such as a keyboard, for inputting data, the visual alarm can be displayed via the traditional screen.

While the alert module 124 has been described as generating visual and/or audible alerts, alternatively or additionally, the alert module 124 may include a biofeedback algorithm. The biofeedback algorithm can allow the alert module to control one or more operating parameters in of the ECBT machine 120 in accordance with the biofeedback algorithm by adjusting the one or more operating parameters such that the estimated UFR is reduced.

In the foregoing description, embodiments of the invention have been described with reference to numerous specific details that may vary from implementation to implementation. The description and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising," in the foregoing description or following claims, what follows this phrase can be an additional step or entity, or a sub-step/sub-entity of a previously-recited step or entity.

What is claimed is:

1. A medical device, comprising
   a display device;
   a computer-readable medium comprising computer-executable instructions;
   one or more processors configured to execute the computer-executable instructions;
   an alert module configured to be communicatively coupled to the one or more processors and produce an alert; and
   one or more sensor devices communicatively coupled to the one or more processors;
   wherein, when the one or more processors are executing the computer-executable instructions, the one or more processors are configured to carry out operations to:
   receive, from the one or more sensor devices, one or more values associated with a user of the medical device, the one or more values comprising a current weight of the user;
   determine an estimated post-treatment ultrafiltration rate based on the one or more values;
   compare the estimated post-treatment ultrafiltration rate to an ultrafiltration rate threshold value; and
   in response to determining that the estimated post-treatment ultrafiltration rate exceeds the ultrafiltration rate threshold value, adjusting one or more operating parameters of the medical device.

2. The medical device of claim 1, wherein the one or more values associated with the user comprises a target dry weight of the user.

3. The medical device of claim 1, wherein the one or more values associated with the user comprises an additional volume of fluid entering the user's body during a treatment session.

4. The medical device of claim 1, wherein the one or more values associated with the user comprises an ultrafiltration time.

5. The medical device of claim 1, wherein the medical device is a dialysis machine.

6. The medical device of claim 1, wherein the ultrafiltration rate threshold value is 13.0 mL/kg/hr.

7. The medical device of claim 1, wherein the one or more processors are configured to dynamically determine the estimated post-treatment ultrafiltration rate while the user is undergoing treatment with the medical device.

8. The medical device of claim 1, wherein the one or more processors are configured to determine the estimated post-treatment ultrafiltration rate according to the formula:

$$\frac{(\text{Current Weight} - \text{DryWeightTarget}) * 1000 + \text{AdditionalFluidVolume}}{\text{UFTime} * \text{DryWeightTarget}},$$

wherein CurrentWeight is the current weight of the user, Dry Weight Target is a target weight for the user after undergoing treatment, AdditionalFluidVolume is an estimated volume of fluid the user may receive during treatment, and UFTime is an amount of time the user will undergo treatment.

9. The medical device of claim 1, wherein the one or more sensor devices comprise a weight sensor coupled to a seat portion of the medical device.

10. A method, comprising:
    receiving, from one or more sensor devices, one or more values associated with a user of a medical device, the one or more values comprising a current weight of the user;
    determining an estimated post-treatment ultrafiltration rate based on the one or more values;
    comparing the estimated post-treatment ultrafiltration rate to an ultrafiltration rate threshold value; and
    in response to determining that the estimated post-treatment ultrafiltration rate exceeds the ultrafiltration rate threshold value, adjusting one or more operating parameters of the medical device.

11. The method of claim 10, wherein the one or more values associated with the user comprises a target dry weight of the user.

12. The method of claim 10, wherein the one or more values associated with the user comprises an additional volume of fluid entering the user's body during a treatment session.

13. The method of claim 10, wherein the one or more values associated with the user comprises an ultrafiltration time.

14. The method of claim 10, wherein the one or more sensor devices comprise a weight sensor coupled to a seat portion of the medical device.

15. The method of claim 10, wherein the ultrafiltration rate threshold value is 13.0 mL/kg/hr.

16. The method of claim 10, wherein the estimated post-treatment ultrafiltration rate is determined dynamically while the user of the medical device is undergoing treatment with the medical device.

17. The method of claim 10, wherein determining a post-treatment ultrafiltration rate comprises using the formula:

$$\frac{(CurrentWeight - DryWeightTarget) * 1000 + AdditionalFluidVolume}{UFTime * DryWeightTarget},$$

wherein CurrentWeight is the current weight of the user, Dry Weight Target is a target weight for the user after undergoing treatment, AdditionalFluidVolume is an estimated volume of fluid the user may receive during treatment, and UFTime is an amount of time the user will undergo treatment.

18. The medical device of claim 1, wherein the operations further comprise:

in response to determining that the estimated post-treatment ultrafiltration rate exceeds the ultrafiltration rate threshold value, controlling at least one of (i) the display device to display a visual alert or (ii) a speaker of the alert module to emit an audible alert.

19. The method of claim 10, further comprising:

in response to determining that the estimated post-treatment ultrafiltration rate exceeds the ultrafiltration rate threshold value, controlling at least one of (i) a display device of the medical device to display a visual alert or (ii) a speaker of an alert module to emit an audible alert.

20. The method of claim 10, wherein adjusting one or more operating parameters of the medical device comprises adjusting the one or more operating parameters to reduce the estimated post-treatment ultrafiltration rate.

* * * * *

UNITED STATES PATENT AND TRADEMARK OFFICE
CERTIFICATE OF CORRECTION

| | |
|---|---|
| PATENT NO. | : 11,738,125 B2 |
| APPLICATION NO. | : 17/320901 |
| DATED | : August 29, 2023 |
| INVENTOR(S) | : Michael Singer et al. |

It is certified that error appears in the above-identified patent and that said Letters Patent is hereby corrected as shown below:

In the Claims

Claim 8
Column 16, Line 25, delete "(Current Weight" and insert --(CurrentWeight--.
Column 16, Line 31, delete "Dry Weight Target" and insert --DryWeightTarget--.

Claim 17
Column 17, Line 9, delete "(Current Weight" and insert --(CurrentWeight--.
Column 17, Line 15, delete "Dry Weight Target" and insert --DryWeightTarget--.

Signed and Sealed this
Thirty-first Day of October, 2023

Katherine Kelly Vidal
*Director of the United States Patent and Trademark Office*